US00PP33135P2

(12) United States Plant Patent
de Groot

(10) Patent No.: US PP33,135 P2
(45) Date of Patent: Jun. 8, 2021

(54) *ROSA* 'RUIRI0126A'

(50) Latin Name: *Rosa hybrida*
Varietal Denomination: RUIRI0126A

(71) Applicant: De Ruiter Intellectual Property B.V., Amstelveen (NL)

(72) Inventor: Hendrikus Cornelis Adrianus de Groot, Amstelveen (NL)

(73) Assignee: De Ruiter Intellectual Property B.V.

( * ) Notice: Subject to any disclaimer, the term of this patent is extended or adjusted under 35 U.S.C. 154(b) by 0 days.

(21) Appl. No.: 16/987,147

(22) Filed: Aug. 6, 2020

(51) Int. Cl.
*A01H 5/02* (2018.01)
*A01H 6/74* (2018.01)

(52) U.S. Cl.
USPC ..... Plt./107

(58) Field of Classification Search
USPC ..... Plt./107
See application file for complete search history.

*Primary Examiner* — Annette H Para
(74) *Attorney, Agent, or Firm* — Cassandra Bright

(57) ABSTRACT

A new and distinct hybrid *Rosa* cultivar named 'RUIRI0126A' is disclosed, characterized by pink-red flowers with a light floral fragrance, and glossy foliage. Plants are upright, and exhibit good resistance to blackspot diseases. The new variety is a *Rosa*, normally produced as an outdoor garden or container plant.

2 Drawing Sheets

Figure 1:
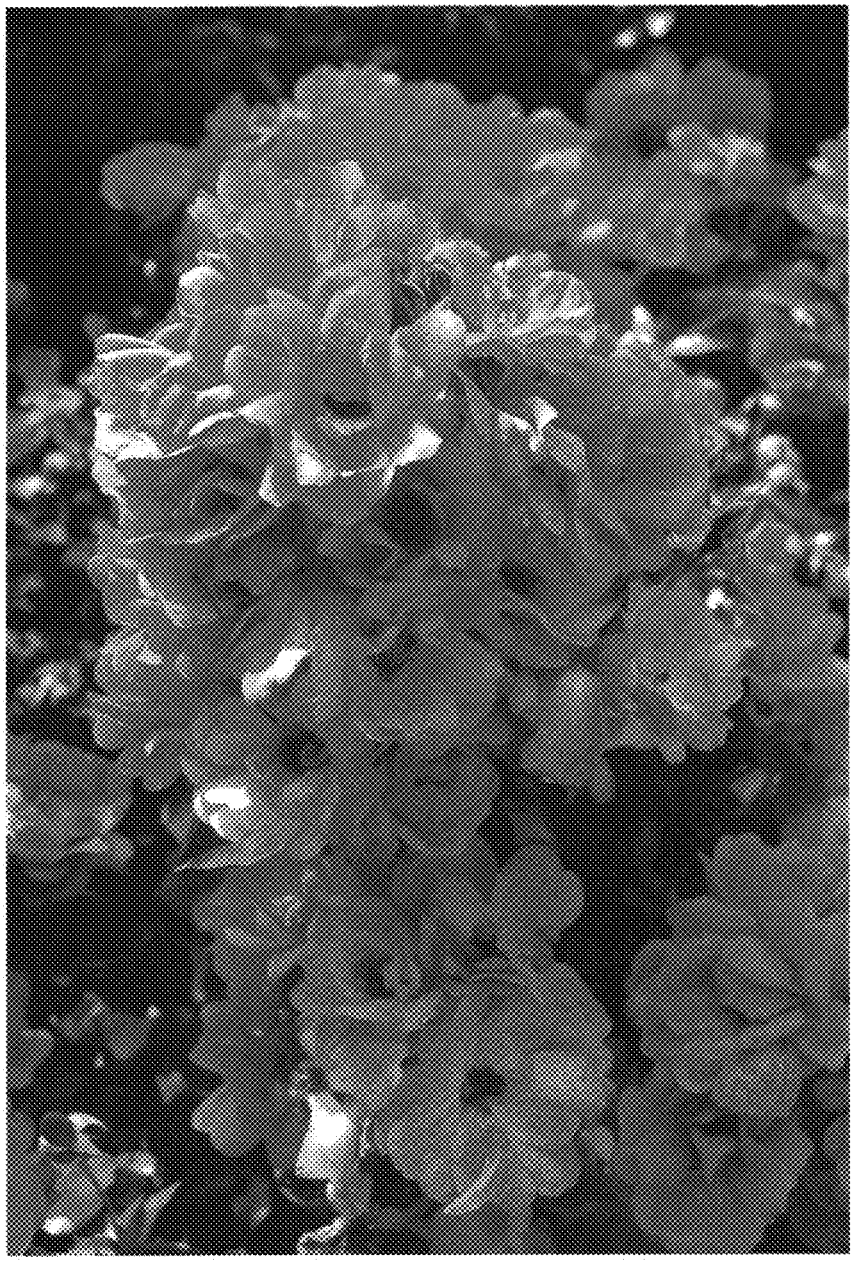

Latin name of the genus and species: *Rosa hybrida.*
Variety denomination: 'RUIRI0126A'.

BACKGROUND OF THE INVENTION

The new *Rosa* cultivar is a product of a planned breeding program conducted by the inventor. The cross resulting in this new variety was made May 2008 at a research nursery in Hazerswoude, the Netherlands.

The seed parent is the unpatented variety *Rosa* 'NOA150097'. The pollen parent is the unpatented variety *Rosa foliolosa* 'RUIBA028B'. The new variety was selected in May 2011 by the inventor at the same research nursery in Hazerswoude, the Netherlands. The inventor continued observing characteristics of the new variety for several years, in the controlled conditions of the research nursery.

Asexual reproduction of the new cultivar was performed by vegetative softwood cuttings. This was first performed at a greenhouse in Amstelveen, the Netherlands, in May 2013, and has shown that the unique features of this cultivar are stable and reproduced true to type in successive generations.

SUMMARY OF THE INVENTION

The cultivar 'RUIRI0126A' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RUIRI0126A' These characteristics in combination distinguish 'RUIRI0126A' as a new and distinct *Rosa* cultivar:

1. Dark pink flowers.
2. Highly abundant flowering.
3. Glossy foliage.
4. Suitability for landscape and groundcover use.
5. Flowering continuously from June until October in the Netherlands.

PARENTAL COMPARISON

Plants of the new cultivar 'RUIRI0126A' are similar to plants of the seed parent, in most horticultural characteristics, however, plants of the new cultivar 'RUIRI0126A' differ in the following:

1. The new variety has dark pink flowers, while the seed parent has light red flowers.
2. The new variety has glossier leaf.

Plants of the new cultivar 'RUIRI0126A' are similar to plants of the pollen parent in most horticultural characteristics, however, plants of the new cultivar 'RUIRI0126A' differs in the following;

1. The new variety is a floribunda type, the pollen parent is a multiflora type.
2. The new variety has pink-red flowers while the pollen parent has white flowers.
3. The pollen parent develops a rose hip fruit not seen in the new variety.

COMMERCIAL COMPARISON

Plants of the new cultivar 'RUIRI0126A' can be compared to the commercial variety *Rosa* 'Noatraum', U.S. Plant Pat. No. 7,282. These varieties are similar in most horticultural characteristics, however 'RUIRI0126A' differs in the following:

1. This new cultivar has larger flowers than this comparator.
2. This new cultivar has a more upright plant habit than this comparator.

Plants of the new cultivar 'RUIRI0126A' can be compared to the commercial variety *Rosa* 'Korselary', unpatented. These varieties are similar in most horticultural characteristics, however 'RUIRI0126A' differs in the following:

1. This new cultivar has darker pink flowers than this comparator.
2. This new cultivar has a more compact plant habit than this comparator.

BRIEF DESCRIPTION OF THE PHOTOGRAPHS

The accompanying photograph in FIG. 1 illustrates a close-up view of a typical inflorescence.

Figure 2:
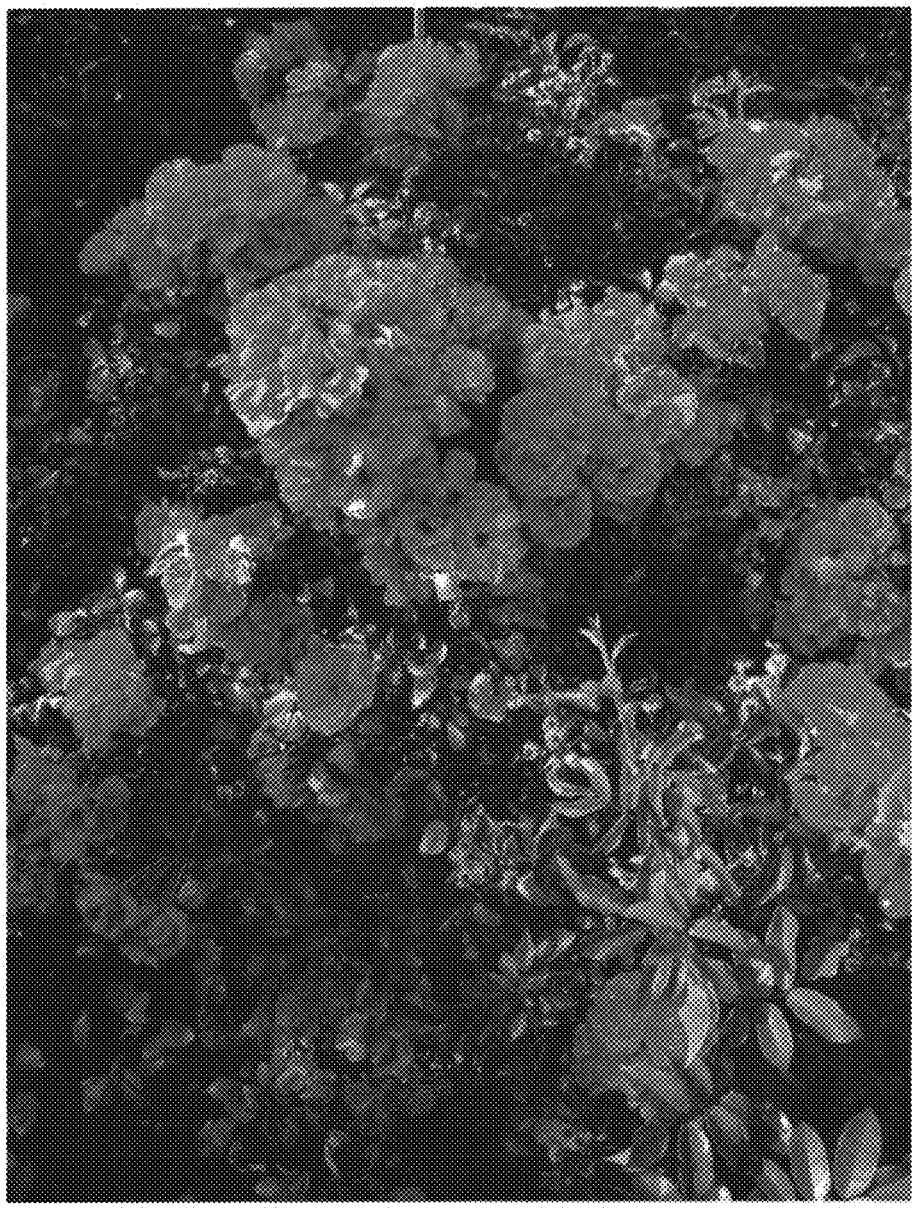

FIG. 2 illustrates in full color typical plants of 'RUIRI0126A' grown in the ground at a nursery in De Kwakel, The Netherlands. Plants in FIG. 2 are approximately 2 years old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'RUIRI0126A' plants grown outdoors, in De Kwakel, The Netherlands. The growing temperature ranged from approximately 20° C. to 26° C. during the day and from approximately 16° C. to 18° C. during the night. Measurements were taken in August. General light conditions were very bright, normal sunlight. Measurements and numerical values represent averages of typical plant types.

Botanical classification: *Rosa* 'RUIRI0126A'.

Market classification: Landscape/groundcover multiflora.

PROPAGATION

Time to initiate roots: 10 days at approximately 25° C.

Time to produce a rooted cutting: 21 days at approximately 25° C.

Typical method: Vegetative terminal cuttings, does not require grafting.

PLANT

Growth habit: Intermediate.

Age of plant described: 2 years.

In a container or in the ground: Ground.

Height: 65 cm.

Plant spread: 50 cm.

Rootstock: Own roots.

Branching characteristics:

Length of primary lateral branches: Approximately 24 cm.

Diameter of lateral branches: Approximately 4 cm.

Quantity of lateral branches: 4 to 8 main laterals.

Branching arrangement: Compound.

Branches-young wood:

- *Diameter*.—Approximately 0.3 cm.
- *Texture*.—Smooth.
- *Approximately density/quantity of thorns*.—Moderate.
- *Color*.—Near RHS Yellow-Green 146D.

Branches-old wood:

- *Diameter*.—Approximately 0.9 cm, after 0.5 years.
- *Color*.—Near RHS Yellow-Green 146B.
- *Texture*.—Smooth.
- *Approximate density/quantity of thorns*.—Dense.
- *Thorns*.—Color: Near RHS Grey-Brown 199A. Height: 1.2 cm. Diameter: 0.9 cm.

FOLIAGE

Leaf:

- *Arrangement*.—Imparipinnate.
- *Quantity*.—Approximately 7 per main branch.
- *Average length*.—Approximately 10 cm.
- *Average width*.—Approximately 6 cm.

Leaflet:

- *Quantity*.—3, 5, or 7 per leaf.
- *Average length*.—Approximately 4 cm.
- *Average width*.—Approximately 2.5 cm.
- *Shape of blade*.—Ovate.
- *Apex*.—Obtuse.
- *Base*.—Cordate.
- *Margin*.—Serrate.
- *Texture of top surface*.—Smooth.
- *Texture of bottom surface*.—Smooth.
- *Leaf internode length*.—3.5-4 cm.
- *Color*.—Young foliage upper side: Near RHS Green 137C. Young foliage under side: Near RHS Yellow-Green 146B. Mature foliage upper side: Near RHS Green NN137A. Mature foliage under side: Near RHS Green 137C.
- *Venation*.—Type: Pinnate. Venation color upper side: Near RHS Green 137C. Venation color under side: Near RHS Green 137D.

Stipule:

- *Length*.—1.2 cm.
- *Width*.—0.7 cm.
- *Color*.—Near RHS Green 137C.
- *Texture*.—Smooth.

Petiole:

- *Length*.—1.2 cm.
- *Width*.—0.2 cm.
- *Color*.—Near RHS Green 137C.
- *Texture*.—Hairy.

Rachis:

- *Length*.—1.4 cm.
- *Width*.—0.2 cm.
- *Color*.—Near RHS Green 137D.
- *Texture*.—Pubescent.

FLOWER

Natural flowering season: June-October in Europe.

Begins flowering after how many years/months: 2 months.

Inflorescence type: Multiflora.

Rate of flower opening: Approximately 3 days from bud to fully opened flower.

Flower longevity on plant: 7 days, after fully opened.

Quantity of flowers: 12 flowers per inflorescence.

Inflorescence size:

- *Diameter*.—Approximately 13 cm.
- *Length*.—Approximately 12 cm.

Flower size:

- *Diameter*.—Approximately 6 cm.
- *Length*.—Approximately 3.2 cm.

Peduncle:

- *Length*.—3.5 cm.
- *Diameter*.—0.2 cm.

Petals:

- *Petal arrangement*.—Rotate, loose.
- *Length*.—3 cm.
- *Width*.—2.5 cm.
- *Shape*.—Obcordate.
- *Margin*.—Undulate.
- *Apex*.—Retuse.
- *Base*.—Cuneate.
- *Petal quantity*.—20.
- *Texture*.—Velvet.
- *Color*.—When opening: Upper surface: Near RHS Red-Purple N66A. Lower surface: Near RHS Red-Purple 67C. Fully opened: Upper surface: Near RHS Red-Purple N66A. Lower surface: Near RHS Red-Purple 67C.

Bud:
*Shape*.—Ovate.
*Length*.—Approximately 1.5 cm.
*Diameter*.—Approximately 1 cm.
*Color*.—Near RHS Red-Purple 60C.
Sepals:
*Length*.—1.5 cm.
*Width*.—0.6 cm.
*Shape*.—Lanceolate.
*Color*.—Interior Surface: Near RHS Green 137D, margin White 155D. Exterior Surface: Near RHS Green 137C.
*Texture*.—Smooth.
Receptacle:
*Length*.—0.9 cm.
*Width*.—0.5 cm.
*Shape*.—Ovate.
*Color*.—Near RHS Yellow-Green 144D.
Fragrance: None.

REPRODUCTIVE ORGANS

Stamens:
*Quantity*.—Average 60.
*Filament length*.—Average 0.5 cm.
*Filament color*.—Near RHS Greyed-Orange N167D.
Anthers:
*Length*.—2 mm.
*Shape*.—Oblong.
*Color*.—RHS Yellow-Orange 22A.
*Pollen*.—Color: Near RHS Greyed-Orange 177D. Quantity: Sparse.
Pistil:
*Number*.—20.
*Length*.—6 mm.
*Style*.—Length: Approximately 0.5 cm. Color: Near RHS Yellow-Green 149D.
Stigma:
*Shape*.—Orbicular.
*Color*.—RHS Greyed-Yellow 160D.

OTHER CHARACTERISTICS

Seeds and fruits: Not observed.
Seeds and fruits: Not observed.
Disease/pest resistance: Neither resistance nor susceptibility to typical diseases and pests of landscape roses observed.
Temperature tolerance: USDA zones 4-9.

What is claimed is:

1. A new and distinct hybrid cultivar of *Rosa* plant named 'RUIRI0126A' as herein illustrated and described.

* * * * *